United States Patent
Zhang et al.

(10) Patent No.: US 12,193,759 B2
(45) Date of Patent: Jan. 14, 2025

(54) REAL-TIME CORRECTION OF REGIONAL TISSUE DEFORMATION DURING ENDOSCOPY PROCEDURE

(71) Applicant: Canon U.S.A., Inc., Melville, NY (US)

(72) Inventors: Hualei Shelley Zhang, Brookline, MA (US); Brian Ninni, Woburn, MA (US)

(73) Assignee: Canon U.S.A., Inc., Melville, NY (US)

( * ) Notice: Subject to any disclaimer, the term of this patent is extended or adjusted under 35 U.S.C. 154(b) by 83 days.

(21) Appl. No.: 17/564,844

(22) Filed: Dec. 29, 2021

(65) Prior Publication Data

US 2022/0202501 A1 Jun. 30, 2022

Related U.S. Application Data

(60) Provisional application No. 63/132,163, filed on Dec. 30, 2020.

(51) Int. Cl.
| | |
|---|---|
| *A61B 34/20* | (2016.01) |
| *A61B 5/00* | (2006.01) |
| *A61B 34/10* | (2016.01) |
| *G06T 19/00* | (2011.01) |
| *G06T 19/20* | (2011.01) |

(52) U.S. Cl.
CPC ............ *A61B 34/20* (2016.02); *A61B 5/7264* (2013.01); *A61B 34/10* (2016.02); *G06T 19/003* (2013.01); *G06T 19/20* (2013.01); *A61B 2034/105* (2016.02); *A61B 2034/107* (2016.02); *A61B 2034/2055* (2016.02); *G06T 2210/41* (2013.01); *G06T 2219/2004* (2013.01)

(58) Field of Classification Search
None
See application file for complete search history.

(56) References Cited

U.S. PATENT DOCUMENTS

| | | |
|---|---|---|
| 6,671,538 B1 | 12/2003 | Ehnholm et al. |
| 8,320,991 B2 | 11/2012 | Jascob et al. |
| 9,138,165 B2 | 9/2015 | Holsing et al. |
| 9,782,223 B2 | 10/2017 | Ross |
| 9,854,991 B2 | 1/2018 | Bzostek et al. |
| 10,144,637 B2 | 12/2018 | Bai et al. |
| 10,575,907 B2 | 3/2020 | Dekel et al. |
| 10,639,105 B2 | 5/2020 | Razeto et al. |

(Continued)

OTHER PUBLICATIONS

Scott W. Sinclair, et al., Airway Strain during Mechanical Ventilation in an Intact Animal Model, American Journal of Respiratory and Critical Care Medicine, Oct. 15, 2007, pp. 786-794. vol. 176, No. 8.

(Continued)

*Primary Examiner* — Patricia J Park
(74) *Attorney, Agent, or Firm* — Canon U.S.A., Inc. I.P. Division

(57) ABSTRACT

A method for visualization guidance of device-to-image registration includes acquiring image data of a patient, generating a 3D model of the anatomy of the patient based on the image data, performing initial registration between image space and device space, advancing a device into a structure, tracking trajectory of the device in relation to the model, determining divergence between the device trajectory and the model, and effecting correction to the model or the device trajectory to minimize the divergence.

23 Claims, 9 Drawing Sheets

(56) References Cited

U.S. PATENT DOCUMENTS

| | | | |
|---|---|---|---|
| 10,706,543 B2 | 7/2020 | Donhowe et al. | |
| 10,846,893 B2 | 11/2020 | Weingarten et al. | |
| 2016/0070436 A1* | 3/2016 | Thomas | G06T 7/0012 |
| | | | 715/771 |
| 2016/0314246 A1* | 10/2016 | Roberge | G16H 30/20 |
| 2017/0309026 A1* | 10/2017 | Sakamoto | G06T 7/0016 |
| 2018/0085173 A1* | 3/2018 | Dickhans | A61B 34/20 |
| 2019/0054618 A1* | 2/2019 | Mönnich | B25J 9/163 |
| 2019/0239868 A1* | 8/2019 | Attenborough | A61F 2/28 |
| 2020/0139125 A1* | 5/2020 | Noble | A61B 5/1072 |
| 2020/0390503 A1* | 12/2020 | Casas | A61B 34/20 |
| 2021/0169578 A1* | 6/2021 | Calloway | A61B 34/25 |
| 2021/0169583 A1* | 6/2021 | Gleiman | A61B 5/065 |
| 2022/0156925 A1* | 5/2022 | Bydlon | G06T 7/149 |

OTHER PUBLICATIONS

Michael A. Pritchett et al., Virtual or reality: divergence between preprocedural computed tomography scans and lung anatomy during guided bronchoscopy, Journal of Thoracic Disease, Jan. 6, 2020, pp. 1595-1611.

Michael A. Pritchett et al., Cone-Beam CT With Augmented Fluoroscopy Combined With Electromagnetic Navigation Bronchoscopy for Biopsy of Pulmonary Nodules, Journal of Bronchology & Interventional Pulmonology, Oct. 2018, pp. 274-282, vol. 25, No. 4.

* cited by examiner

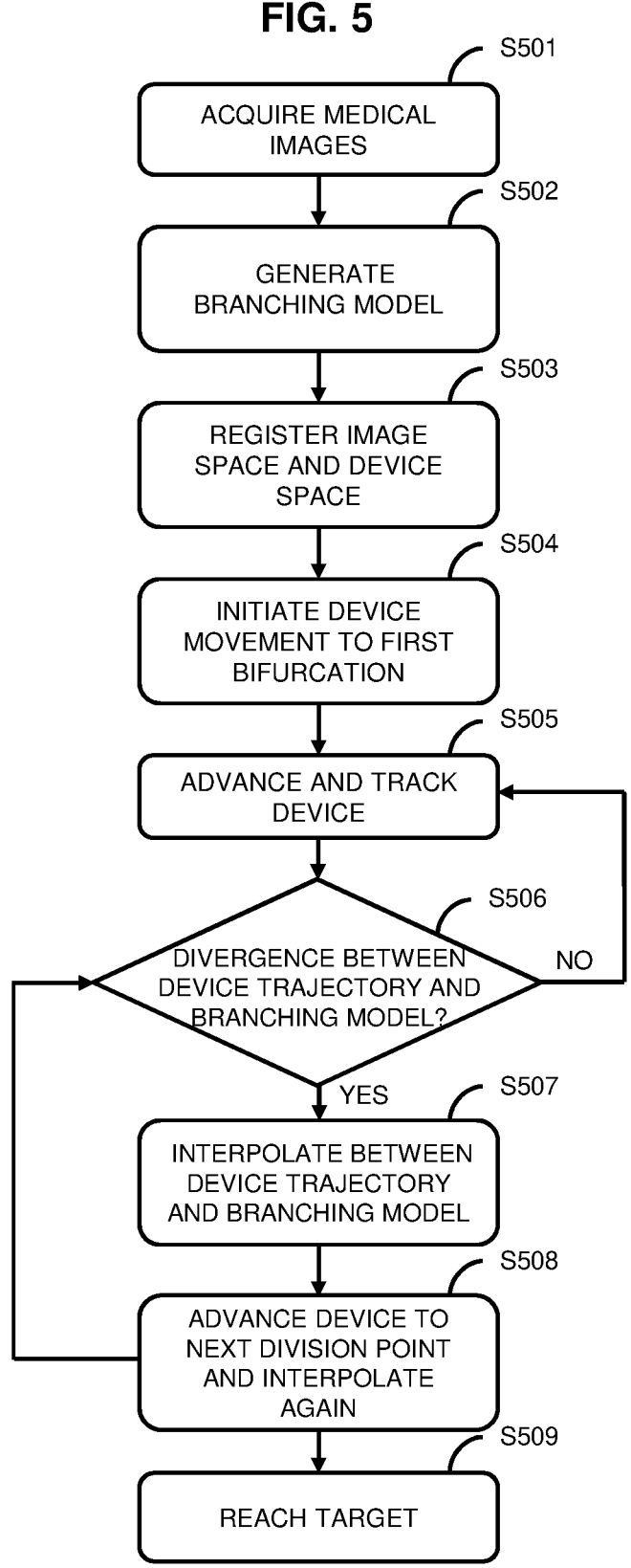

REAL-TIME CORRECTION OF REGIONAL TISSUE DEFORMATION DURING ENDOSCOPY PROCEDURE

CROSS REFERENCE TO RELATED APPLICATIONS

The present application claims the benefit of priority from U.S. Provisional Application No. 63/132,163 filed Dec. 30, 2020, which is hereby incorporated by reference herein in its entirety.

BACKGROUND

Field of the Disclosure

The present disclosure generally relates to medical imaging and, more particularly, to a method, apparatus, and medium for visualization guidance of device-to-image registration during an endoscopy procedure.

Description of the Related Art

During an image guided surgical procedure, an instrument such as an endoscopic catheter device glides into a patient. Medical images such as CT, MRI, or the like, can be used to capture patient anatomy a priori, and serve as a source to generate a three-dimensional guidance map. A catheter device may have an electromagnetic sensor on the tip and a position of the catheter device tip in the patient can be detected by a detector which may be provided outside of the patient's body. A successful image-guided procedure is generally based on accurate registration or proper alignment between the patient anatomy in image space and catheter position in device space. An image stack of the patient anatomy provides a snapshot of an internal branching structure which however is deformable and has circumferential and longitudinal strains as high as 100% and 60%, respectively, under mechanical ventilation.

Proper image-guidance depends on the ability to set up registration between device space and image space. However, a number of factors may contribute to mismatch between the device space and image space throughout the procedure including, for example, breathing and bulk motions, as well as the pulling and stretching interaction of the catheter with the interior sidewall, particularly when the endoscopic device travels in narrow branches or tortuous curves.

Any deviation of a guidance map with an actual branching structure leads to an incorrect overlay of catheter position relative to the map, which compromises the guiding capability from pre-procedural image models.

A system and method for respiratory-gated point cloud for soft tissue navigation disclosed in Holsing (U.S. Pat. No. 9,138,165) describes the correction of respiratory motion, which is the partial contribution of the branching structure deformation. Other factors include pulling and stretching interactions between the endoscopic device and the branching structure, which is irrelevant to respiratory cycles.

A system and method described in Pritchett ("Cone-Beam CT with Augmented Fluoroscopy Combined with Electromagnetic Navigation Bronchoscopy for Biopsy of Pulmonary Nodules", J Bronchol Intervent Pulmonol, Volume 25, Number 4, October 2018) for overlaying three-dimensional Cone-Beam Computed Tomography data on live fluoroscopy (augmented fluoroscopy) with automatic positional adaptation can track the anatomical movement during the procedure, however, introduces continuous radiation exposure and equipment constraints.

A need exists to overcome these concerns and provide enhanced visualization guidance of device-to-image registration during an endoscopy procedure.

SUMMARY

The present disclosure provides real-time correction of regional tissue deformation during an endoscopy procedure through visualization guidance of device-to-image registration during an endoscopy procedure.

According to some embodiments, a method for visualization guidance of device-to-image registration includes acquiring image data of a patient, generating a 3D model of the anatomy of the patient based on the image data, performing initial registration between image space and device space, advancing a device into a structure, tracking trajectory of the device in relation to the model, determining divergence between the device trajectory and the model, and effecting correction to the model or the device trajectory to minimize the divergence.

Further features of the present disclosure will become apparent from the following description of exemplary embodiments with reference to the attached drawings, where like structure is indicated with like reference numerals.

BRIEF DESCRIPTION OF THE DRAWINGS

FIG. 4, which includes

FIG. 5 is a flow chart according to some embodiments.

DESCRIPTION OF THE EMBODIMENTS

Various exemplary embodiments, features, and aspects of the disclosure will be described below with reference to the drawings.

In the present disclosure, one or more configurations are described that functionally implement real-time correction of regional tissue deformation during an endoscopy procedure with imaging modalities including, for example, CT (computed tomography), MRI (magnetic resonance imaging), IVUS (intravascular ultrasound), PET (positron emission tomography), X-ray imaging, combinations or hybrids thereof, or the like. Configurations may be configured to facilitate placement of medical tools, catheters, needles or the like, and may be free standing, patient mounted, or the like. The present disclosure is not limited to any particular configuration.

According to some embodiments, the present disclosure may be configured to obtain medical image data from one or more imaging arrangements configured to implement image processing for visual guidance of device-to-image registration during an endoscopy procedure.

The device-to-image registration processing according to some embodiments can implement functioning through use of one or more processes, techniques, algorithms, or the like, that can provide real-time correction of regional tissue deformation through the visualization guidance of the device-to-image registration during the endoscopy procedure.

Figure 1:
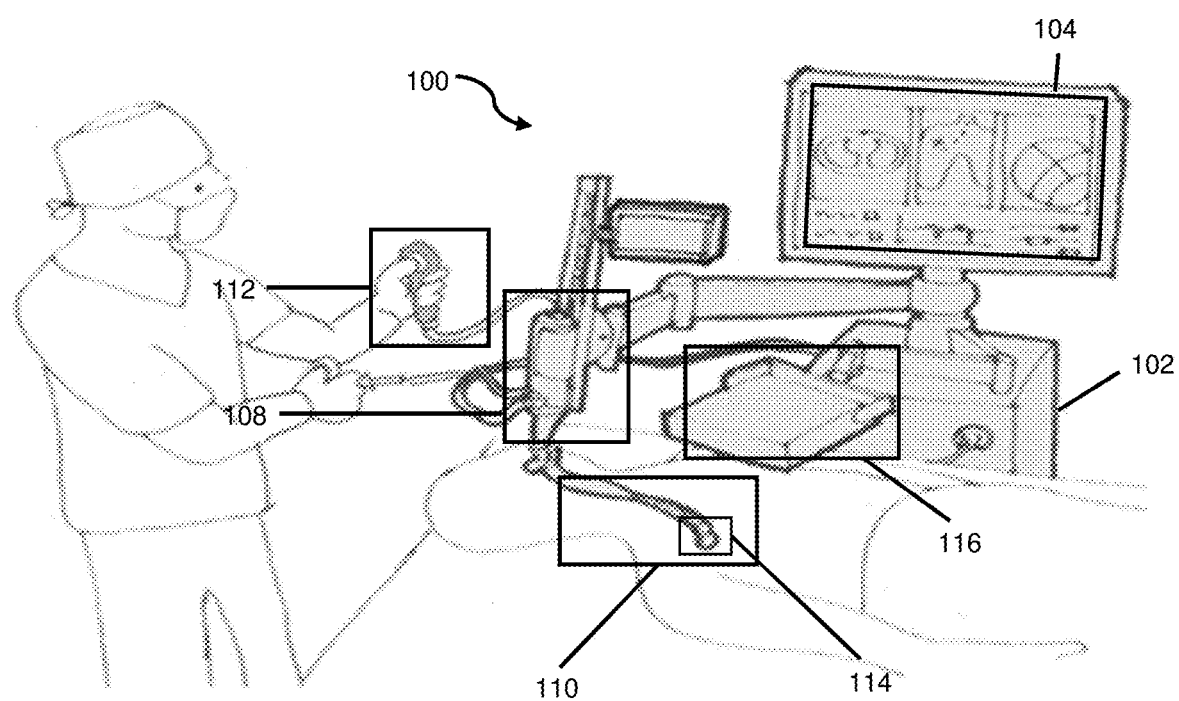
FIG. 1 illustrates an exemplary endoscopic apparatus configuration according to some embodiments.
Figure 2:
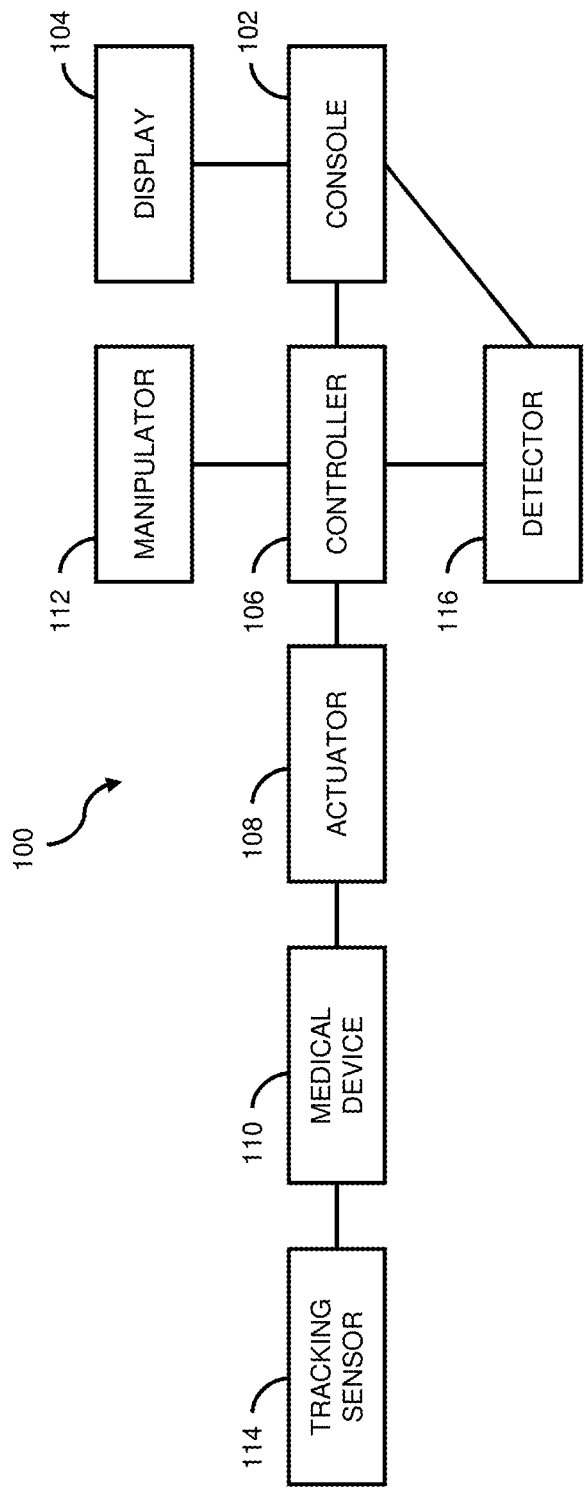
FIG. 2 is a block diagram of an endoscopic apparatus according to some embodiments.

FIG. 1 illustrates an exemplary endoscopic apparatus or configuration 100 according to some embodiments. FIG. 2 shows a hardware configuration of the apparatus 100.

The apparatus 100 can include one or more of a console 102, a display 104, a controller 106, an actuator 108, a medical device 110, a manipulator 112, a tracking sensor 114, and a detector 116, and can include other elements or components. Throughout the present disclosure, the medical device 110 is referred to as a "catheter", but one or more of a variety of other types, configurations, or arrangements also fall within the scope of the present disclosure including, for example, a sheath, guidewire, needle, probe, forceps, or the like.

The console 102 executes software, computer instructions, algorithms, or the like, and controls to display a navigation screen on the display 104. The console 102 may generate a three-dimensional (3D) model of an internal branching or non-branching structure, for example, lungs or other internal structures, of a patient based on medical images such as CT, MRI, or the like. Alternatively, the 3D model may be received by the console 102 from another device.

The console 102 acquires catheter position information from the controller 106. Alternatively, the console 102 may acquire the catheter position information directly from the detector 116.

The console 102 generates and outputs the navigation screen to the display 104 based on the 3D model and the catheter positional information by executing the software. The navigation screen can indicate a current position of the catheter 110 on the 3D model. By the navigation screen, a user can recognize the current position of the catheter 110 in the structure.

The console 102 executes a correction of the acquired 3D model based on the catheter positional information so as to minimize a divergence between the catheter position and a path mapped out on the 3D model, as described below.

According to some embodiments, the model can be a branching or non-branching model, and the structure can be a branching or non-branching structure. The correction to the model or the device trajectory to minimize the divergence can include curve fitting through interpolations including linear interpolation, piecewise linear interpolation, nonlinear interpolation, or other types of correction.

The console 102 can determine a route to a target, arrive at the target, and perform a medical procedure.

Figure 3:
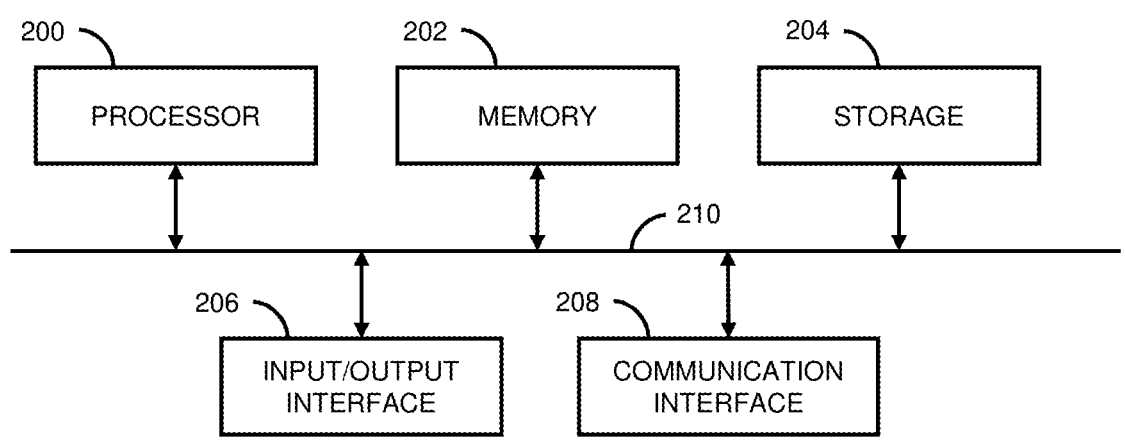
FIG. 3 is a block diagram of a console or a controller according to some embodiments.

The console 102 operates to control the elements of the apparatus 100 and has one or more configurational components that include, as shown in FIG. 3, one or more of a processor 200, a memory 202, a storage 204, an input and output (I/O) interface 206, and communication interface 208. The apparatus 100 can be interconnected with medical instruments or a variety of other devices, and can be controlled independently, externally, or remotely by the console 102 and/or controller 106.

The processor 200 can be configured as a control circuit or circuitry for performing overall control of the apparatus 100, and can execute a program, instructions, code or software stored in the memory 202 and/or storage 204 to perform various data processing, computation, algorithmic tasks, or other functions of the apparatus 100. The memory 202 and/or can store the program, software, computer instructions, information, other data, or combinations thereof. The memory 202 is used as a work memory. The processor 200, which may include one or more processors, circuitry, or a combination thereof, executes the software developed in the memory 202. The I/O interface 206 inputs the catheter positional information to the console 102 and outputs information for displaying the navigation screen to the display 104.

The display 104 may be a display device configured, for example, as a monitor, an LCD (liquid-crystal display), an LED (light-emitting diode) display, an OLED (organic LED) display, a plasma display, an organic electro luminescence panel, or the like. Based on the control of the apparatus, the navigation screen may be displayed on the display 104 showing one or more images being captured, captured images, captured moving images recorded on the storage unit, or the like.

The components are connected together by a bus 210 so that the components can communicate with each other. The bus 210 transmits and receives data between these pieces of hardware connected together, or transmits a command from the processor 200 to the other pieces of hardware. The components can be implemented by one or more physical devices that may be coupled to the processor 200 through a communication channel. For example, the console 102 and/or controller 106 can be implemented using circuitry in the form of ASIC (application specific integrated circuits) or the like. Alternatively, the console 102 and/or controller 106 can be implemented as a combination of hardware and software, where the software is loaded into a processor from a memory or over a network connection. Functionality of the console 102 and/or controller 106 can be stored on a storage medium, which may include RAM (random-access memory), magnetic or optical drive, diskette, cloud storage, or the like.

In the embodiments below, the navigation screen is generated by the software but it may be generated by firmware.

Figures 4A, 4B:
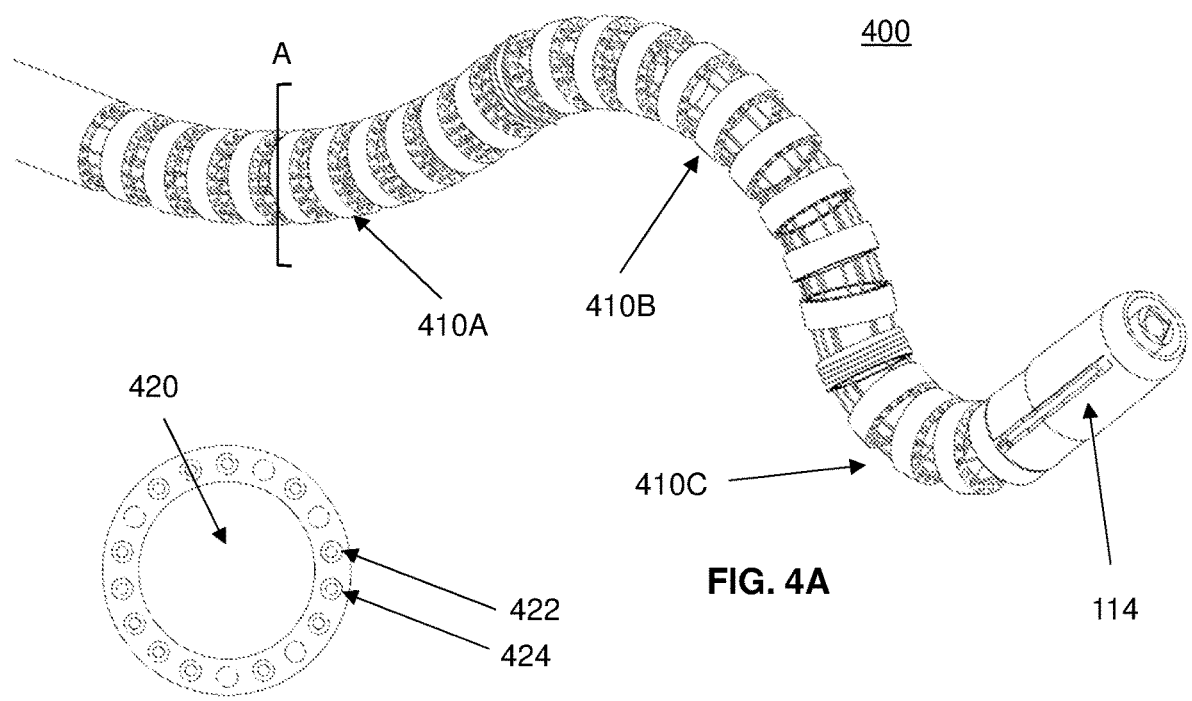
FIGS. 4A and 4B, illustrates a catheter configuration according to some embodiments.

FIG. 4, which includes FIGS. 4A and 4B, shows an embodiment of the medical device 110 configured as a catheter 400.

In FIG. 4A, the catheter 400 includes a proximal section 410A, a middle section 410B, and a distal section 410C. The catheter 400 includes a plurality of driving wires 422 and supporting wires 424 that are in a lumen surrounding a central hollow chamber 420, as shown in the cross-sectional view of FIG. 4B.

Each of the proximal section 410A, middle second 410B, and distal section 410C, can be bent by a plurality of driving wires 422 (driving liner members) as driving backbones. The posture of the catheter 400 can be maintained by supporting wires 424 (supporting liner members) as passive sliding backbones. The driving wires 422 are connected to actuator 108. The actuator 108 may include one or more motors and drives each section of the catheter 400 by pushing and/or pulling the driving wires.

The tracking sensor 114 can be an electromagnetic tracking sensor (EM tracking sensor) and is attached to the tip of the catheter device 110.

The detector 116 detects a position of the EM tracking sensor 114 and outputs the detected positional information to the controller 106.

The controller 106 receives the positional information of the catheter tip from the detector 116. The controller 106 controls the actuator 108 in accordance with the manipulation by a user via one or more manipulator 112.

The controller 106 can control the catheter device 110 based on an algorithm known as follow-the-leader (FTL) algorithm. By applying the FTL algorithm, the middle section and the proximal section (following sections) of the catheter device 110 move at a first position in the same way as the distal section moved at the first position or a second position near the first position.

According to some embodiments, a method for visualization guidance of device-to-image registration includes acquiring image data of a patient, generating a 3D model of the anatomy of the patient based on the image data, performing initial registration between image space and device space, advancing a device into a structure, tracking trajectory of the device in relation to the model, determining divergence between the device trajectory and the model, and effecting correction to the model or the device trajectory to minimize the divergence.

According to some embodiments, the model can be a branching or non-branching model, and the structure can be a branching or non-branching structure. The correction to the model or the device trajectory to minimize the divergence can include curve fitting through interpolations including linear interpolation, piecewise linear interpolation, nonlinear interpolation, or other types of correction.

The method can determine a route to a target, arrive at the target, and perform a medical procedure.

FIG. 5 illustrates a first embodiment of a method for visualization guidance of device-to-image registration according the present disclosure. The apparatus 100 of FIGS. 1-3 can implement the first embodiment. The steps can be performed by executing a software read from storage 204 by the processor 200.

First, the medical images of the patient are acquired in step S501 prior to the procedure. Imaging modality can be MRI, CT or any tomography that acquires the three-dimensional anatomy. Next, a model is generated where segmentation of model, delineation of target tissue as well as generation of routes to target are part of step S502. The model can be a branching or non-branching model, and the structure can be a branching or non-branching structure.

The image space and device space are then registered in step S503 at the beginning of the procedure so a universal coordinate system can be used to utilize the model as guidance map. Movement of the medical device 110 is initiated at step S504 at the beginning of the navigation phase, and the medical device 110 is advanced to the first bifurcation, up to which is assumed to have negligible deviation between image space and device space. The medical device 110 moves or advances in step S505, and as the device 110 continues to advance along the desired route, the trajectory of the location of the device tip and orientation is stored in memory.

In step S506, a determination is made as to whether there is any divergence between the previously generated model and the potentially deformed structure in the anatomy. The detection of the divergence can be broken down to two possible scenarios: a) if within the same branch, the device location departs circumferentially and is outside the branch; and b) if traversing through a bifurcation or trifurcation, the device physically enters the correct sub-branch but is not reflected on the virtual map of the model. In a case where no divergence is detected, the device 110 continues the path forward in step S505. Otherwise, the correction process begins in step S507. The correction to the model or the device trajectory to minimize the divergence can include curve fitting through interpolations including linear interpolation, piecewise linear interpolation, nonlinear interpolation, or other types of correction. The console 102 can determine a route to a target, arrive at the target, and perform a medical procedure. Once the device 110 reaches the next division point, i.e., bifurcation or trifurcation, the segment between previous and current division points is re-aligned within the model and the device trajectory in step S508. The process continues until the device 110 reaches the desired proximity to the target tissue in step S509 and performs a medical procedure as desired, such as a biopsy, treatment delivery (e.g. ablation, drug delivery, etc.), or other types of medical procedures.

Figure 6:
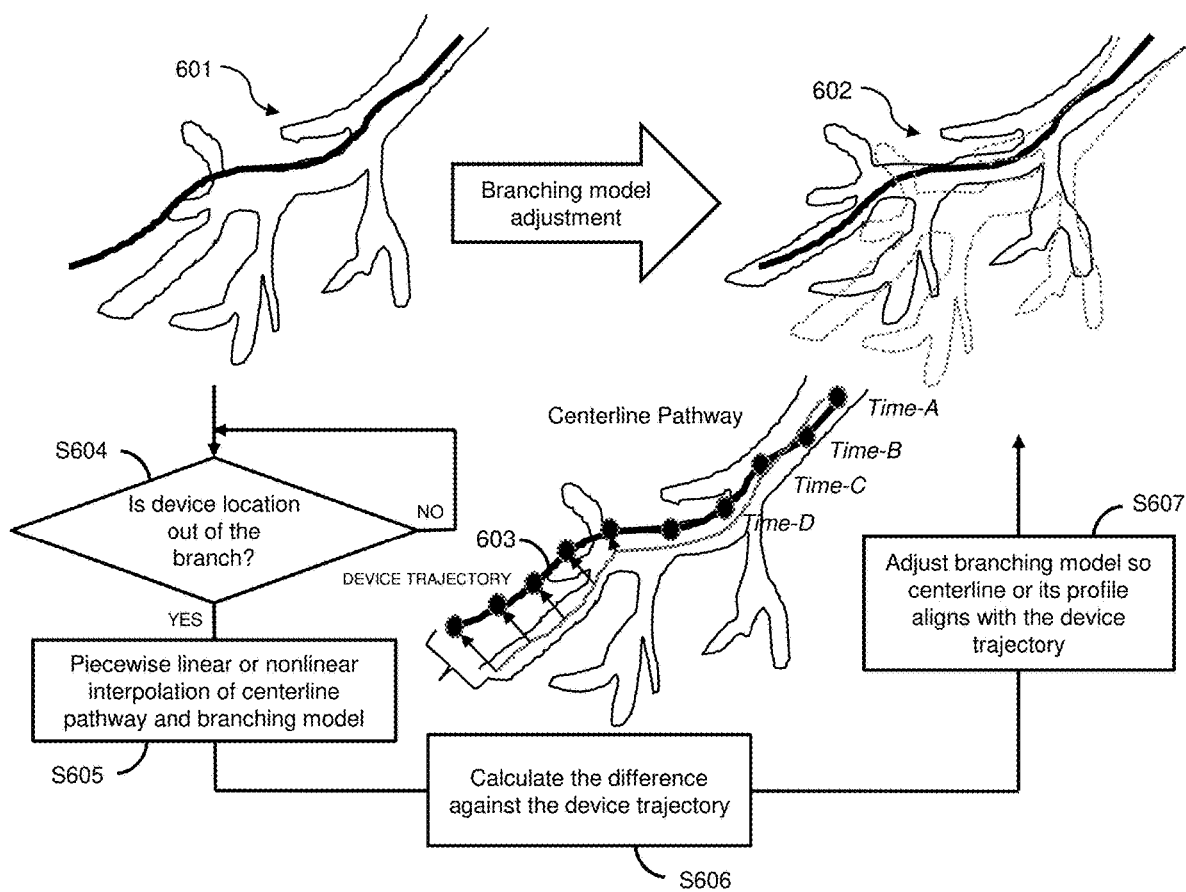
FIG. 6 is a model workflow according to some embodiments.

Some embodiments of converging the device trajectory and the model in step S507 is to adjust the model so to minimize the divergence between the model and the device trajectory, as shown in FIG. 6. The model, superimposed with the device trajectory is represented by 601. The actual route of the catheter is acquired based on readings of the tracking sensor on the tip of the device. If the tracked location is outside the model on the virtual map at step S604, curve fitting of the centerline pathway and subsequently the model is performed at step S605 by assuming continuous small-step motions from Time-A to Time-B, from Time-B to Time-C, from Time-C to Time-D, etc. in 603. The correction to minimize the divergence can include curve fitting through interpolations including linear interpolation, piecewise linear interpolation, nonlinear interpolation, or other types of correction. The console 102 can determine a route to a target, arrive at the target, and perform a medical procedure.

Through calculating the error difference and iterative corrections to minimize the differences in step S606, the process completes when the centerline pathway or the profile of the branching model is aligned with the device trajectory based on results of the calculations in step S607 so that the adjusted model has superimposed device trajectory bounded within branches 603.

Figure 7:
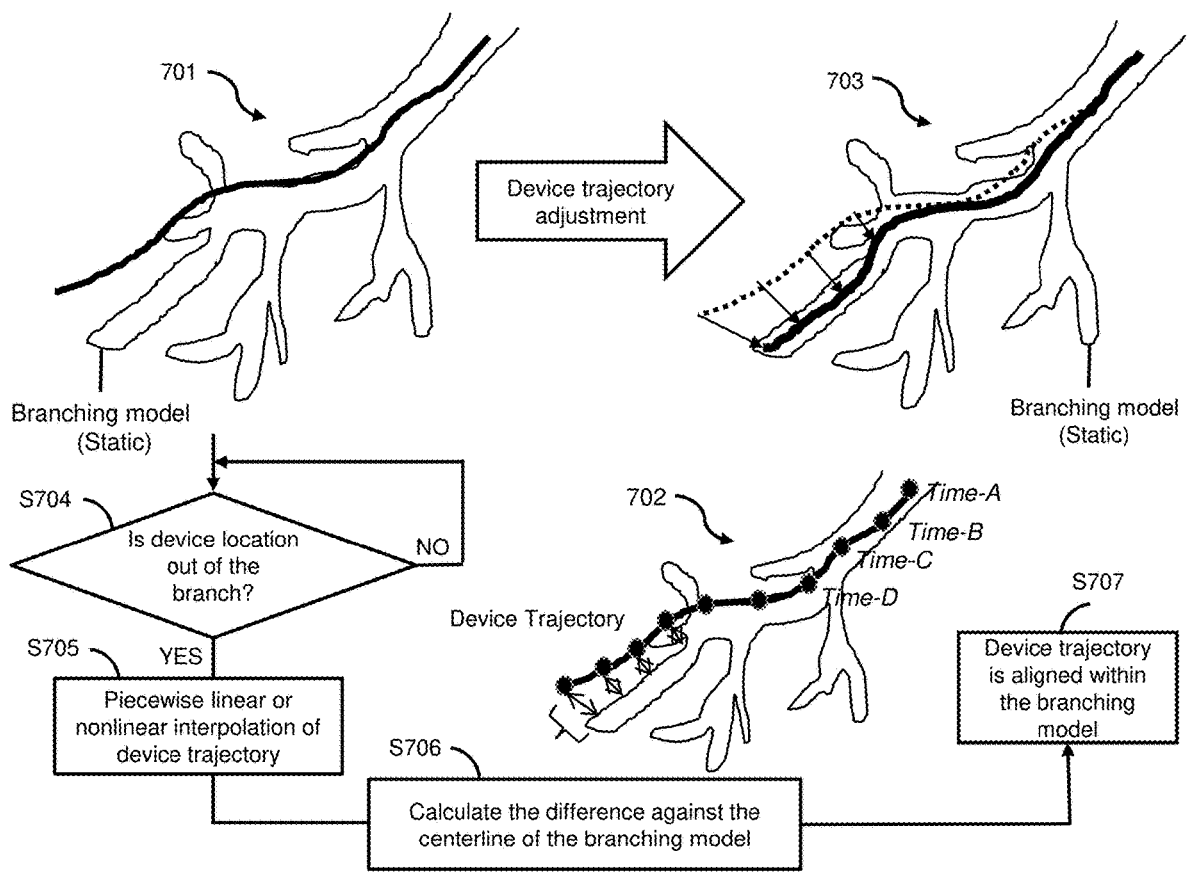
FIG. 7 is a device trajectory workflow embodiment according to some embodiments.

Some embodiments of converging the device trajectory and the model in step S507 is to adjust the device trajectory so to minimize the divergence between model and device trajectory, as shown in FIG. 7. The static model, superimposed with device trajectory is depicted by 701. The actual route of the catheter is acquired based on readings of the tracking sensor on the tip of the device. When the device location is detected outside of the branch on the virtual view map in step S704, curve fitting through interpolations including linear interpolation, piecewise linear interpolation, nonlinear interpolation, or other types of correction of the trajectory is performed in step S705 by assuming continuous small-step motions from Time-A to Time-B, from Time-B to Time-C, from Time-C to Time-D, etc. 702. Through calculating the error difference and iterative corrections to minimize the differences in step S706, the device trajectory is adjusted based on the calculation results so that the device is bounded within the model in step S707 and serves as guidance on the virtual map 703.

Figure 8:
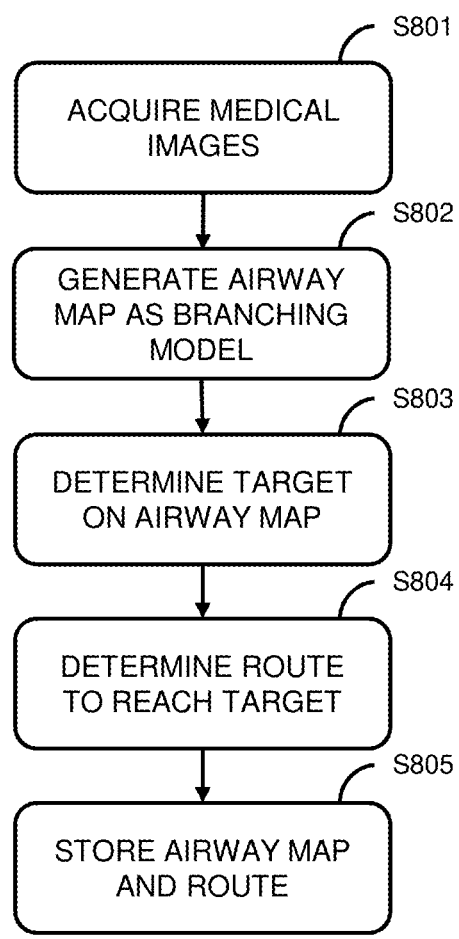
FIG. 8 is a flow chart of planning of a medical device as a catheter according to some embodiments.

FIG. 8 shows steps of planning of an a priori phase of a medical device as a catheter operation. These steps are performed by executing a software read from the storage 204 by the processor 200.

In step S801, medical images such as CT, MRI images are acquired.

In step S802, a three-dimensional model of a structure (for example, an airway model of lungs) is generated based on the acquired medical images. The model can be a branching or non-branching model, and the structure can be a branching or non-branching structure.

In step S803, a target on the airway model is determined based on a user instruction.

In step 804, a route of the catheter device to reach the target on the branching structure of the airway model is determined based on a user instruction.

In step 805, the generated airway model and decided route on the airway model is stored in the storage 204 or the memory 202.

In this way, a 3D model of a branching structure is generated and a target and a route on the 3D model is determined and stored before the catheter operation is started.

Figure 9:
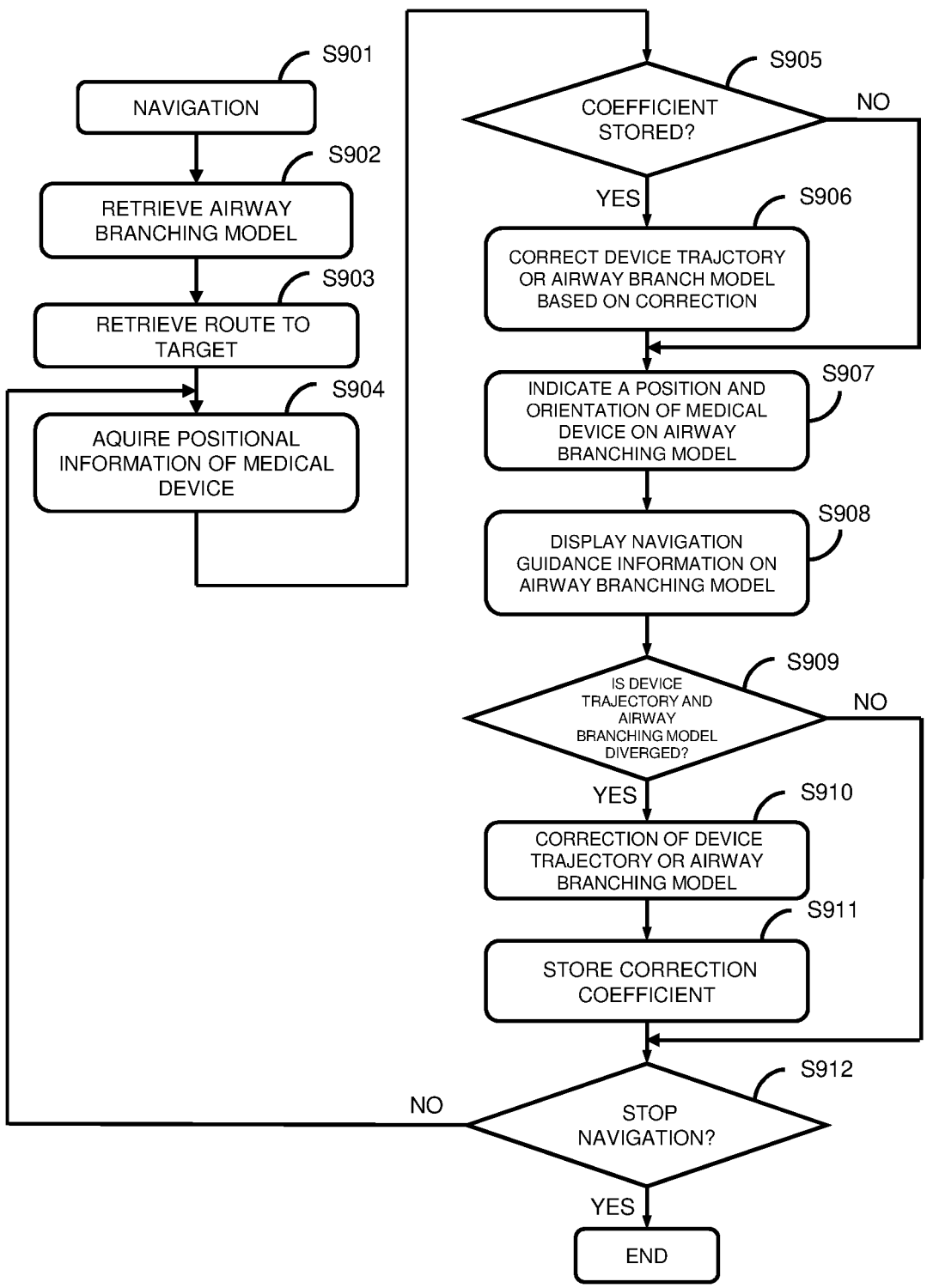
FIG. 9 is a flow chart according to some embodiments.

FIG. 9 shows a workflow of correction of an airway model performed during the catheter operation according to some embodiments. These steps are performed by executing software read from the storage 204 by processor 200. The model (for example, an airway branching model) is adjusted as shown in FIG. 6. Alternatively, some embodiments of adjusting a display of a trajectory of catheter device 110 is shown in FIG. 7.

In step S901, the processor 200 begins the navigation phase based on data previously acquired during the a priori phase.

In step S902, the processor 200 retrieves the airway model stored in the storage 204 or memory 202.

In step S903, the processor 200 retrieves the route to the target stored in the storage 204 or memory 202.

In step S904, the processor 200 acquires positional information of the tip of the catheter from the controller 106 or detector 114.

In step S905, the processor 200 determines whether a correction coefficient for the airway model is stored in the memory 202 or storage 204. The correction coefficient is a coefficient used to correct the airway model or the device trajectory. The airway of a patient deforms because of breathing, bulk movement or interactive forces between the catheter device and the interior sidewall, creating a gap between shapes of the airway model and actual airway of the patient. The correction coefficient is to correct a shape of the airway model to match with a shape of the current airway shape of the patient. Alternatively, the correction coefficient is used to correct the display of trajectory of the catheter device 110 in the airway model to align the catheter device 110 within the airway of the patient. The coefficient is generated at step S909 and is stored at step S910. If the correction coefficient to be applied is stored, then it moves to step S906. If the correction coefficient to be applied is not stored, then it moves to step S907.

In step S906, the processor 200 corrects the device trajectory or the airway branch model based on the correction.

In step S907, the processor 200 indicates a position and orientation of the catheter tip of the medical device on the airway model on the display 104.

In step S908, the processor 200 displays navigation guidance information on the airway model which is displayed on the display 104.

In step S909, the processor 200 determines whether the device trajectory and the airway model diverged. The processor 200 determines that the device trajectory and the airway model diverged if the catheter goes across a boundary of the airway and the tip of the catheter is outside of the airway model. Alternatively, the processor 200 may determine that the device trajectory and the airway model diverged if the catheter device 110 goes a right way as planned at every junction of the airway but it looks like the catheter device 110 is swerving from the planned course.

In step S910, the processor 200 corrects or adjusts the device trajectory or the airway branching model of the catheter device 110. The processor 200 can correct or adjust the device trajectory or the airway branching model of the catheter device 110 in the way described in the above embodiments. The correction to the model or the device trajectory to minimize the divergence can include curve fitting through interpolations including linear interpolation, piecewise linear interpolation, nonlinear interpolation, or other types of correction.

In step S911, the processor 200 stores the correction coefficient. The correction coefficient corresponds to an amount of adjustment of each point of the airway branching model or the trajectory of the catheter device 110.

In step S912, the processor 200 determines whether the navigation of the catheter device 110 ends. For example, if a user inputs an instruction to stop the navigation, the processor 200 determines that the navigation of the catheter device 110 ends. If the processor 200 determines that the navigation does not end, then it moves to step S904. If the processor 200 determines that the navigation ends, the processor 200 ends the navigation sequence.

Additional features or aspects of present disclosure can also advantageously implement one or more AI (artificial intelligence) or machine learning algorithms, processes, techniques, or the like, to implement real-time correction of regional tissue deformation during an endoscopy procedure through visualization guidance of device-to-image registration during an endoscopy procedure. Such AI techniques use a neural network, a random forest algorithm, a cognitive computing system, a rules-based engine, or the like, and are trained based on a set of data to assess types of data and generate output. For example, a training algorithm can be configured to provide accurate registration or proper alignment between the patient anatomy in image space and catheter position in device space. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the medical images of detailed positional configurations of the patient anatomy relative to the catheter position can be used as input data and provided to the training algorithm. Initial images, output values and detailed positional configurations of the catheter position relative to the patient anatomy can be stored in a database to facilitate precise real-time correction of regional tissue deformation during an endoscopy procedure for new data. Through visualization guidance of device-to-image registration that are generated using input mapping to the model(s) or through expert research, machine learning can find parameters for AI processes. The training algorithm is configured to learn physical relationships in the input data to best describe these relationships or correlations. The data sets include information based on a number of factors including, for example, the acquired images, the number of acquired images, the angle of the image, the position of the image, detailed positional configurations of the medical device relative to the branching model, or the like. The data is evaluated using a weighted evaluation where the weights are learned through a training process, through subject matter specifications, or the like. Deep learning mechanisms can augment an AI process to identify indicators in the image data that can include, for example, new data images, output values or positional configurations of the catheter position relative to the patient anatomy, or the like.

According to some embodiments, a method for visualization guidance of device-to-image registration includes acquiring image data of a patient, generating a 3D model of the anatomy of the patient based on the image data, performing initial registration between image space and device space, advancing a device into a structure, tracking trajectory of the device in relation to the model, determining divergence between the device trajectory and the model, and effecting correction to the model or the device trajectory to minimize the divergence.

According to some embodiments, the model can be a branching or non-branching model, and the structure can be a branching or non-branching structure. The correction to minimize the divergence can include curve fitting through interpolations including linear interpolation, piecewise linear interpolation, or nonlinear interpolation.

The method can further include determining a route to a target, arriving at the target, and performing a medical procedure.

Through use of real-time correction of divergence between image space and device space during an endoscopy procedure according to some embodiments, advantages arise including, for example, that the tracking of the device location is in high temporal and spatial resolution, which enables real-time and accurate comparison between static branching model and derived centerline pathway to detect deviation.

The correction can be done real-time by piecewise linear interpolation due to assumptions of small-step motions between time points.

Flexibility of choices between adjusting the branching model or the device trajectory. In addition, instead of using the centerline for adjusting the model registration, a profile of the segmentation can also be used. This would 'remap' the position of the catheter to be along the wall of the lumen, rather than the center of it. A possible reason for this deviation of the tracked sensor leaving the segmented boundary would be in a case where the catheter was scraping against the wall.

The advantage of adjusting the branching model is close to reality, where tissue regional deformation introduces divergence to the static branching model.

The advantage of adjusting the device trajectory is to confine the computation complexity to one-dimension and therefore increasing the computation speed.

Help to lift dependence on live imaging mode such as fluoroscopy.

The main function of live imaging is to provide real-time update of the tissue anatomy as guidance for endoscopy procedure, however, it increases equipment cost and complexity as well as substantial radiation exposure.

The present disclosure provides features of device tracking in high spatial and temporal resolution. The high spatial resolution enables accuracies of device location tracking. The high temporal resolution enables assumption of small-step continuous motion.

The device sensor offers feedback on device location and tip orientation. The feedback of device location is useful for detecting divergence between deformed tissue anatomy and the branching model. Deviation detection can also be used to notify the user if they are travelling down an unmapped lumen. For example, if the software detects a sharp deviation outside of the boundary of the segmentation when there is no bifurcation nearby, it could be due to the user turning into a lumen that was never segmented in the branching model.

The feedback of tip orientation is valuable when determining forward or backward motion trajectory.

Detecting initiation of device trajectory departure from a regional branch.

During the endoscopic navigation, the detection of device departure sets a trigger point to apply the adjustment computation to model or device trajectory.

By generating a synthetic branching model, the adjusted model restores the relative relation between regional branch and device location and provides closer-to-reality map for procedural guidance.

By generating synthetic device trajectory, the adjusted device trajectory provides virtual endoscopic view with interpolated device locations within the regional branch of the branching model.

The converged information can be displayed, and the superimposed view of model and device location provides visualization guidance for endoscopic navigation.

Further distinguishing features of the present disclosure include distinguishing forward and backward motions. In the journey of navigating inside branching structures, the switching between backward and forward motions can produce weaving trajectory, which hinders direct interpolation. Therefore, computing unidirectional travel trajectory can be valuable guidance for endoscopic navigation.

Through storage and application of the correction coefficient, the correction coefficient is a coefficient used to adjust the shape of the airway model or the display of trajectory of the catheter device to match with the current position of the catheter device in the airway of the patient. The memory stores and applies the coefficient throughout steps of positional information update from tracking system.

Various modifications and alterations based on the present disclosure may become apparent to those skilled in the art, and the features of the present disclosure may be applied to one or more configurational arrangements including, for example, CT, MRI, IVUS, PET, X-ray imaging, combinations or hybrids thereof, or the like.

Some embodiments can advantageously implement one or more AI (artificial intelligence) or machine learning algorithms, processes, techniques, or the like, to monitor a sensor of the medical apparatus to obtain a sensor reading, perform impact detection based on the sensor reading, generate an impact profile based on the impact detection, characterize the impact detection, and respond to the impact detection as described above or otherwise contribute to facilitate precision impact profile generation and impact detection. Such AI techniques use a neural network, a random forest algorithm, a cognitive computing system, a rules-based engine, or the like, and are trained based on a set of data to assess types of data and generate output. For example, a training algorithm can be configured to facilitate monitoring a sensor of the medical apparatus to obtain a sensor reading, performing impact detection based on the sensor reading, generating an impact profile based on the impact detection, characterizing the impact detection, and responding to the impact detection. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the sensor monitoring of the medical apparatus to obtain a sensor reading, impact detection based on the sensor reading, generating an impact profile based on the impact detection, characterization of the impact detection, and response to the impact detection can be used as input data and provided to the training algorithm. Sensor readings can be stored in a database to facilitate impact profile and impact detection that are generated using input mapping to the model(s) or through expert research, and machine learning can find parameters for AI processes. Impact profile and impact detection data from the initial data sets are used or placed into an AI process or algorithm to facilitate impact profile and impact detection for new data. The training algorithm is configured to learn physical relationships in the input data to best describe these relationships or correlations. The data sets include information based on a number of factors including, for example, the acquired sensor readings, characterization of the impact detection, and response to the impact detection, or the like. The data is evaluated using a weighted evaluation where the weights are learned through a training process, through subject matter specifications, or the like. Deep learning mechanisms can augment an AI process to identify indicators in the sensor readings that can include, for example, the acquired sensor readings, characterization of the impact detection, and response to the impact detection, or the like.

The algorithm(s) described herein is a set of computer executable instructions that are executed by a medical apparatus. The apparatus can be interconnected with medical instruments or a variety of other devices, and may be controlled independently, externally, or remotely through components including, for example, one or more processors, one or more I/O components, and storage. The one or more processors include one or more central processing units (CPUs), which may include one or more microprocessors (e.g., a single core microprocessor, a multi-core microprocessor); one or more graphics processing units (GPUs); one or more tensor processing units (TPUs); one or more application-specific integrated circuits (ASICs); one or more field-programmable-gate arrays (FPGAs); one or more digital signal processors (DSPs); or other electronic circuitry (e.g., other integrated circuits). The I/O components include communication components (e.g., a graphics card, a network-interface controller) that communicate with a display device and a network, and other input or output devices (not illustrated), which may include a keyboard, a mouse, a printing device, a touch screen, a light pen, an optical-storage device, a scanner, a microphone, a drive, and a game controller (e.g., a joystick, a gamepad).

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A method for visualization guidance of device-to-image registration by an apparatus with at least a device, a display, and a controller, the method comprising:
executing instructions in the controller to cause the apparatus to perform device-to-image registration by:
acquiring image data of a patient;
generating a three-dimensional (3D) model of the anatomy of the patient based on the image data;
performing segmentation of the model into division points;
performing initial registration between image space and device space;
advancing the device into a structure;
detecting movement of the device through the structure;
tracking trajectory of the device in relation to the model;
displaying, on the display, the model superimposed with the device trajectory of the movement of the device through the structure;
determining divergence between the device trajectory and each division point of the model; and
converging the device trajectory and the model by changing the device trajectory between each division point to effect correction to the device trajectory to minimize the divergence,
wherein, correction to the device trajectory is made to converge the device trajectory and the model by adjusting the device trajectory between each division point so the device is bounded within the model.

2. The method according to claim 1, wherein the model is a branching or non-branching model.

3. The method according to claim 1, wherein the structure is a branching or non-branching structure.

4. The method according to claim 1, wherein the correction to minimize the divergence includes curve fitting through interpolations including linear interpolation, piecewise linear interpolation, or nonlinear interpolation.

5. The method according to claim 1, wherein the controller further causes the apparatus to perform:
determining a route for the device to move to a target;
moving the device to arrive at the target; and
performing a medical procedure.

6. The method according to claim 5, wherein the medical procedure is a biopsy or treatment delivery.

7. The method according to claim 1, wherein the controller further causes the apparatus to perform:
changing the model or the device trajectory to effect correction to the device trajectory through iterations.

8. The method according to claim 1, wherein the controller further causes the apparatus to perform:
changing the model or the device trajectory to effect correction to the device trajectory by determining a correction coefficient.

9. The method according to claim 1, wherein the controller further causes the apparatus to perform artificial intelligence or machine learning to change at least one of the device trajectory or the model to effect correction to the device trajectory.

10. The method according to claim 9, wherein the artificial intelligence or machine learning is iterative.

11. An apparatus for visualization guidance of device-to-image registration, the apparatus comprising:
a device;
a display; and
a controller configured to execute instructions to cause the apparatus to perform device-to-image registration by:
acquiring image data of a patient;
generating a three-dimensional (3D) model of the anatomy of the patient based on the image data;
performing segmentation of the model into division points; performing initial registration between image space and device space;
advancing the device into a structure;
detecting movement of the device through the structure;
tracking trajectory of the device in relation to the model;
displaying, on the display, the model superimposed with the device trajectory of the movement of the device through the structure;
determining divergence between the device trajectory and each division point of the model; and
converging the device trajectory and the model by changing the device trajectory between each division point to effect correction to the device trajectory to minimize the divergence,
wherein, correction to the device trajectory is made to converge the device trajectory and the model by adjusting the device trajectory between each division point so the device is bounded within the model.

12. The apparatus according to claim 11, wherein the model is a branching or non-branching model.

13. The apparatus according to claim 11, wherein the structure is a branching or non-branching structure.

14. The apparatus according to claim 11, wherein the controller further causes the apparatus to perform changing the device trajectory to effect correction to minimize the divergence by curve fitting through interpolations including linear interpolation, piecewise linear interpolation, or nonlinear interpolation.

15. The apparatus according to claim 11, wherein the controller further causes the apparatus to perform:
determining a route for the device to move to a target;
moving the device to arrive at the target; and
performing a medical procedure.

16. The apparatus according to claim 15, wherein the medical procedure is a biopsy or treatment delivery.

17. The apparatus according to claim 11, wherein the controller further causes the apparatus to perform changing the device trajectory to effect correction through iterations.

18. The apparatus according to claim 11, wherein the controller further causes the apparatus to perform determining a correction coefficient.

19. The apparatus according to claim 1, wherein the controller further causes the apparatus to perform artificial intelligence or machine learning to change the device trajectory to effect correction to the device trajectory.

20. The apparatus according to claim 19, wherein the artificial intelligence or machine learning is iterative.

21. A non-transitory storage medium storing a program for causing a computer to execute a method for visualization guidance of device-to-image registration by an apparatus with at least a device, a display, and a controller, the method comprising:
executing instructions in the controller to cause the apparatus to perform device-to-image registration by:
acquiring image data of a patient;
generating a three-dimensional (3D) model of the anatomy of the patient based on the image data;
performing segmentation of the model into division points;
performing initial registration between image space and device space;
advancing the device into a structure;
detecting movement of the device through the structure;
tracking trajectory of the device in relation to the model;
displaying, on the display, the model superimposed with the device trajectory of the movement of the device through the structure;
determining divergence between the device trajectory and each division point of the model; and
converging the device trajectory and the model by changing the device trajectory between each division point to effect correction to the device trajectory to minimize the divergence,
wherein, correction to the device trajectory is made to converge the device trajectory and the model by adjusting the device trajectory between each division point so the device is bounded within the model.

22. The method according to claim 1, wherein the controller further causes the apparatus to perform converging the device trajectory and the model by changing the model to effect correction to the model to minimize the divergence,
wherein, correction to the model is made to converge the device trajectory and the model by adjusting the model to align with the device trajectory.

23. The apparatus according to claim 11, wherein the controller further causes the apparatus to perform converging the device trajectory and the model by changing the model to effect correction to the model to minimize the divergence,
wherein, correction to the model is made to converge the device trajectory and the model by adjusting the model to align with the device trajectory.

* * * * *